United States Patent
Zhong et al.

(10) Patent No.: US 11,194,860 B2
(45) Date of Patent: Dec. 7, 2021

(54) QUESTION GENERATION SYSTEMS AND METHODS FOR AUTOMATING DIAGNOSIS

(71) Applicant: Baidu USA, LLC, Sunnyvale, CA (US)

(72) Inventors: Erheng Zhong, Sunnyvale, CA (US); Chaochun Liu, San Jose, CA (US); Yusheng Xie, Campbell, CA (US); Nan Du, Palo Alto, CA (US); Hongliang Fei, Sunnyvale, CA (US); Yi Zhen, San Jose, CA (US); Yu Cao, Santa Clara, CA (US); Richard Chun Ching Wang, Mountain View, CA (US); Dawen Zhou, Fremont, CA (US); Wei Fan, Sunnyvale, CA (US)

(73) Assignee: Baidu USA LLC, Sunnyvale, CA (US)

( * ) Notice: Subject to any disclaimer, the term of this patent is extended or adjusted under 35 U.S.C. 154(b) by 749 days.

(21) Appl. No.: 15/207,445

(22) Filed: Jul. 11, 2016

(65) Prior Publication Data
US 2018/0011979 A1 Jan. 11, 2018

(51) Int. Cl.
*G06F 16/901* (2019.01)
*G16H 50/70* (2018.01)
(Continued)

(52) U.S. Cl.
CPC ......... *G06F 16/9024* (2019.01); *G16H 10/20* (2018.01); *G16H 50/20* (2018.01); *G16H 50/30* (2018.01); *G16H 50/70* (2018.01)

(58) Field of Classification Search
CPC .... G06F 16/9024; G16H 50/20; G16H 50/30; G16H 10/20; G16H 50/70
(Continued)

(56) References Cited

U.S. PATENT DOCUMENTS

| 7,149,756 B1 * | 12/2006 | Schmitt ................. G06Q 50/22 |
| 7,610,313 B2 | 10/2009 | Kawai |

(Continued)

FOREIGN PATENT DOCUMENTS

| CN | 1423789 A | 6/2003 |
| CN | 104854583 A | 8/2015 |
| CN | 105190634 A | 12/2015 |

OTHER PUBLICATIONS

Non-Final Office Action dated Oct. 17, 2018, in U.S. Appl. No. 15/207,434, (26 pgs).

(Continued)

*Primary Examiner* — Robert A Sorey
*Assistant Examiner* — Kimberly A. Sass
(74) *Attorney, Agent, or Firm* — North Weber & Baugh LLP

(57) ABSTRACT

Systems and methods are disclosed for question generation to obtain more related medical information based on observed symptoms from a patient. In embodiments, possible diseases associated with the observed symptoms are generated by querying a knowledge graph. In embodiments, candidate symptoms associated with the possible diseases are also identified and are combined with the observed symptoms to obtain combined symptom sets. In embodiments, discriminative scores for the candidate symptom sets are determined and candidate symptoms with top discriminative scores are selected. In embodiments, these selected candidate symptoms may be checked for conflicts with observed symptoms and removed from further consideration if a conflict exists. In embodiments, one or more questions may be generated based on the remaining selected candidate systems to aid in collecting information about the patient. In embodiments, the process may be repeated with the updated observed symptoms.

19 Claims, 7 Drawing Sheets

(51) Int. Cl.
*G16H 10/20* (2018.01)
*G16H 50/30* (2018.01)
*G16H 50/20* (2018.01)

(58) Field of Classification Search
USPC .......................................................... 705/2
See application file for complete search history.

(56) References Cited

U.S. PATENT DOCUMENTS

| | | | | |
|---|---|---|---|---|
| 8,019,582 | B2 * | 9/2011 | Iliff ........................ | G06Q 50/22 703/11 |
| 10,409,952 | B2 * | 9/2019 | Chen ....................... | G16H 70/60 |
| 2001/0044795 | A1 | 11/2001 | Cohen | |
| 2003/0037034 | A1 | 2/2003 | Daniels | |
| 2004/0093331 | A1 | 5/2004 | Garner | |
| 2005/0055357 | A1 | 3/2005 | Campbell | |
| 2012/0136853 | A1 | 5/2012 | Kennedy | |
| 2013/0310653 | A1 * | 11/2013 | Zillner ................... | G16H 50/20 600/300 |
| 2014/0012790 | A1 | 1/2014 | Oberkampf | |
| 2014/0181214 | A1 * | 6/2014 | Price ..................... | G06F 9/5066 709/205 |
| 2015/0006492 | A1 | 1/2015 | Wexler | |
| 2015/0142704 | A1 * | 5/2015 | London .................. | G06N 5/022 706/11 |
| 2016/0042134 | A1 | 2/2016 | Takla et al. | |
| 2016/0055409 | A1 * | 2/2016 | Majumdar ............... | G06N 3/04 706/20 |
| 2016/0253370 | A1 | 9/2016 | Song | |

OTHER PUBLICATIONS

Response filed Jan. 17, 2019, in U.S. Appl. No. 15/207,434, (17 pgs).
Office Action dated Aug. 13, 2020, in Chinese Patent Application No. CN 201710183072.8, and the Machine Translation (11 pgs).
Search Report and Written Opinion dated Feb. 3, 2020, in Chinese Patent Application No. CN 201710183072.8. (13 pgs).
Hong et al., "Selection of Specific Symptoms of TCM syndromes of Chronic Fatigue with the Random Forest Method", Journal of Traditional Chinese Medicine, 2010, Vol. 51, No. 7 (5pgs).
Office Action dated Dec. 12, 2020, in Chinese Patent Application No. CN 201710183072.8, and the Machine Translation (13 pgs).
Notice of Allowance and Fee Due, dated May 15, 2019, in U.S. Appl. No. 15/207,434 (8 pgs).
Notice of Allowance and Fee Due, dated Sep. 5, 2019, in U.S. Appl. No. 15/207,434 (8 pgs).

* cited by examiner

200

QUESTION GENERATION SYSTEMS AND METHODS FOR AUTOMATING DIAGNOSIS

TECHNICAL FIELD

The present disclosure relates generally to increasing automation of diagnostics based on observed symptoms of a patient, and more specifically to systems and methods for question generation to obtain more related medical information.

BACKGROUND

Automatic diagnosis can help hospitals accommodate more patients by lowering the workload of doctors and help patients to find appropriate doctors/departments. Ideally, an automatic diagnosis system would collect symptom information from a patient and provide automated diagnosis of disease and/or treatment solutions.

However, patients sometimes mention limited or incomplete information or symptoms, which is not enough to do an accurate diagnosis. Therefore, there is a need for a system and method that can guide a patient to answer/provide more related questions for better automatic diagnosis.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments. Items in the figures are not to scale.

DETAILED DESCRIPTION OF THE PREFERRED EMBODIMENTS

Figure 1:
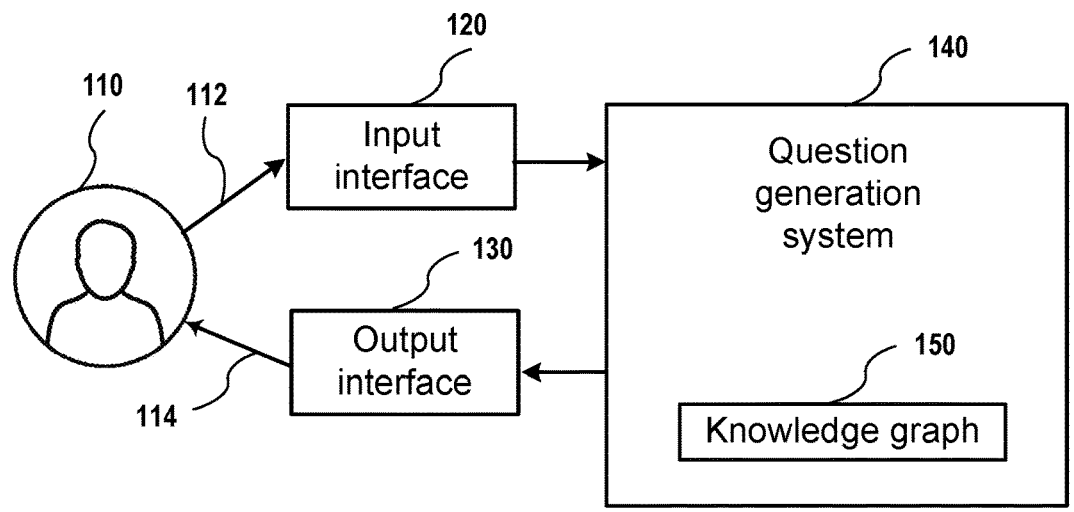
FIG. 1 shows an overall framework for automatic diagnostics according to embodiments of the present disclosure.

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

The terms "include," "including," "comprise," and "comprising" shall be understood to be open terms and any lists the follow are examples and not meant to be limited to the listed items. A set may contain any number of members of the set. Any headings used herein are for organizational purposes only and shall not be used to limit the scope of the description or the claims. Each reference mentioned in this patent document is incorporate by reference herein in its entirety.

Furthermore, one skilled in the art shall recognize that: (1) certain steps may optionally be performed; (2) steps may not be limited to the specific order set forth herein; (3) certain steps may be performed in different orders; and (4) certain steps may be done concurrently.

FIG. 1 depicts an overall framework 100 for helping to automate diagnosis according to embodiments of the present disclosure. In embodiments, a question generation system 140 receives information 112 from a user 110, such as a patient or healthcare worker, via an input interface 120. The question generation system 140 may comprise a knowledge graph 150 for information processing and automatic diagnosis. In embodiments, the knowledge graph 150 may be a standalone component coupling to the question generation system 140 or an integrated part of the question generation system 140. The question generation system 140 may also send questions 114 to the patient via an output interface 130 to obtain more relevant information for more accurate diagnosis.

The information 112 may be one or more patient observed symptoms, such as high fever, coughing, pain, etc. In embodiments, the information 112 may comprise dimensional symptoms having one or more related dimensional information, such as intensity, frequency, duration, etc. Symptom dimension referred to one or more aspects describing a symptom, such as how frequent, how serious, how long, under what condition, where the symptom is observed, etc. This information may be used to aid automatic diagnosis, which may comprise finding symptoms/dimensions to distinguish potential diseases from others, for eliminating irrelevant diseases, and/or generating symptom candidates that are closely related to observed symptoms or other descriptions from or about the patient, etc. The question generation system 140 may be an on-site system or a remote system communicating to the patient through various communication means, such as telephone, Internet, etc. The communication may be a wired or wireless communication.

Figure 2:
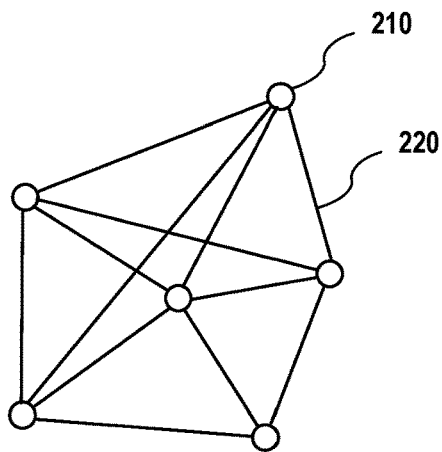
FIG. 2 illustrates an exemplary knowledge graph according to embodiments of the present disclosure.

FIG. 2 depicts an exemplary knowledge graph according to embodiments of the present disclosure. In embodiments, the knowledge graph 200 is a graph encoding domain knowledge, where a node (e.g., node 210) in the graph is an entity, such as a symptom, a dimension, a demographic, and a disease, and an edge (e.g., edge 220) in the graph represents a relationship between two entities. In embodiments, the knowledge graph may couple to external resources, such as various medical database or websites, for knowledge update such that the knowledge graph may be in line with current medical findings. Examples of systems and methods for obtaining symptom-disease correlations, which may be formed into one or more knowledge graph, are found in co-pending and commonly-owned U.S. patent application Ser. No. 15/207,434, filed on Jul. 11, 2016, entitled "SYSTEMS AND METHODS FOR DATA AND INFORMATION SOURCE RELIABILITY ESTIMATION," and listing Yaliang Li, Nan Du, Yusheng Xie, and Wei Fan as inventors, which patent document is incorporated by reference herein in its entirety and for all purposes.

Figure 3:
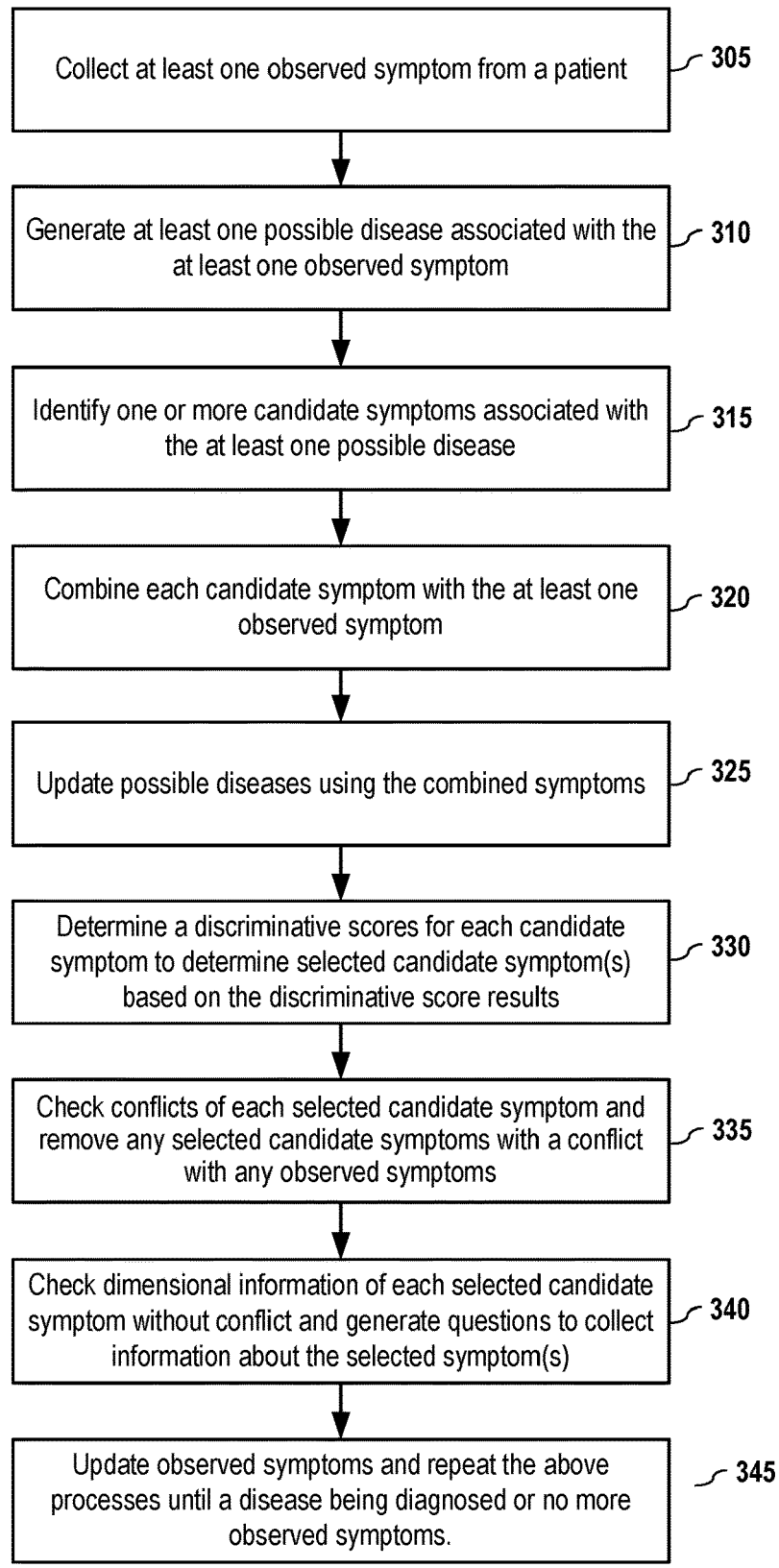
FIG. 3 illustrates an exemplary flow diagram for automatic diagnostics based on collected symptoms according to embodiments of the present disclosure.

FIG. 3 illustrates an exemplary flow diagram for automatic diagnostics based on collected symptoms according to embodiments of the present disclosure. Referring also to FIG. 1, in step 305, a set of one or more observed symptoms ($S_O$) is collected from the patient and input via the input interface. An observed symptom may be a dimensional symptom or a dimensionless symptom. In step 310, a set of one or more possible diseases associated with the set of observed symptoms is generated that associates diseases and symptoms. The generation process may be implemented by querying the knowledge graph.

In step 315, a set of candidate symptoms ($S_C$) associated with the set of possible diseases are identified using the knowledge graph. In embodiments, a candidate symptom may be an unobserved symptom or a symptom not reported to the automatic diagnosis system. In embodiments, a candidate symptom may also be a symptom closely related to an observed symptom or symptoms or other description from the patient.

In step 320, each candidate symptom from the set of candidate symptoms is combined with the set of observed symptoms to get a plurality of combined symptom sets. For example, if the set of candidate symptoms comprises $S_c=\{s_{c_1}, s_{c_2}, s_{c_3}\}$, then three combined symptom sets, $S_1$, $S_2$, and $S_3$ are created in which $S_1=s_{c_1}\cup S_o$, $S_2=s_{c_2}\cup S_o$, and $S_3=s_{c_3}\cup S_o$.

In step 325, in embodiments, using inference from the knowledge graph, the likely (i.e., top ranked) diseases and unlikely diseases (i.e., diseases with a rank below a threshold rank) are identified using the plurality of combined symptom sets. In embodiments, each of the updated likely diseases and unlikely diseases correspond to one combined symptom set.

In step 330, the discriminability (or discriminative score) for each candidate symptom is calculated and used to determine selected candidate symptoms ($S_n$) from the candidate symptoms identified in step 315. In embodiments, the discriminative score is based upon selecting symptoms that have a maximal discriminability in distinguishing between diseases. More details regarding the discriminability calculation will be discussed later. Based upon the discriminability, the top candidate symptoms are selected.

In step 335, the selected candidate symptoms are checked for conflicts with observed symptoms and any selected candidate symptom with a conflict is removed from further consideration. For example, if a symptom relates to males only but the patient is female, that selected candidate system has a conflict and is disregarded. In step 340, the selected candidate symptoms without conflicts are checked for applicable dimension information and questions are generated to collect information about the selected candidate symptoms without conflicts and applicable dimension information. The questions may be generated according to one or more question templates.

Finally, in embodiments, in step 345, the observed symptoms are updated after the information is collected from the generated questions and the above steps may be repeated until a disease is diagnosed or the patient reports no more observed symptoms.

Figure 4:
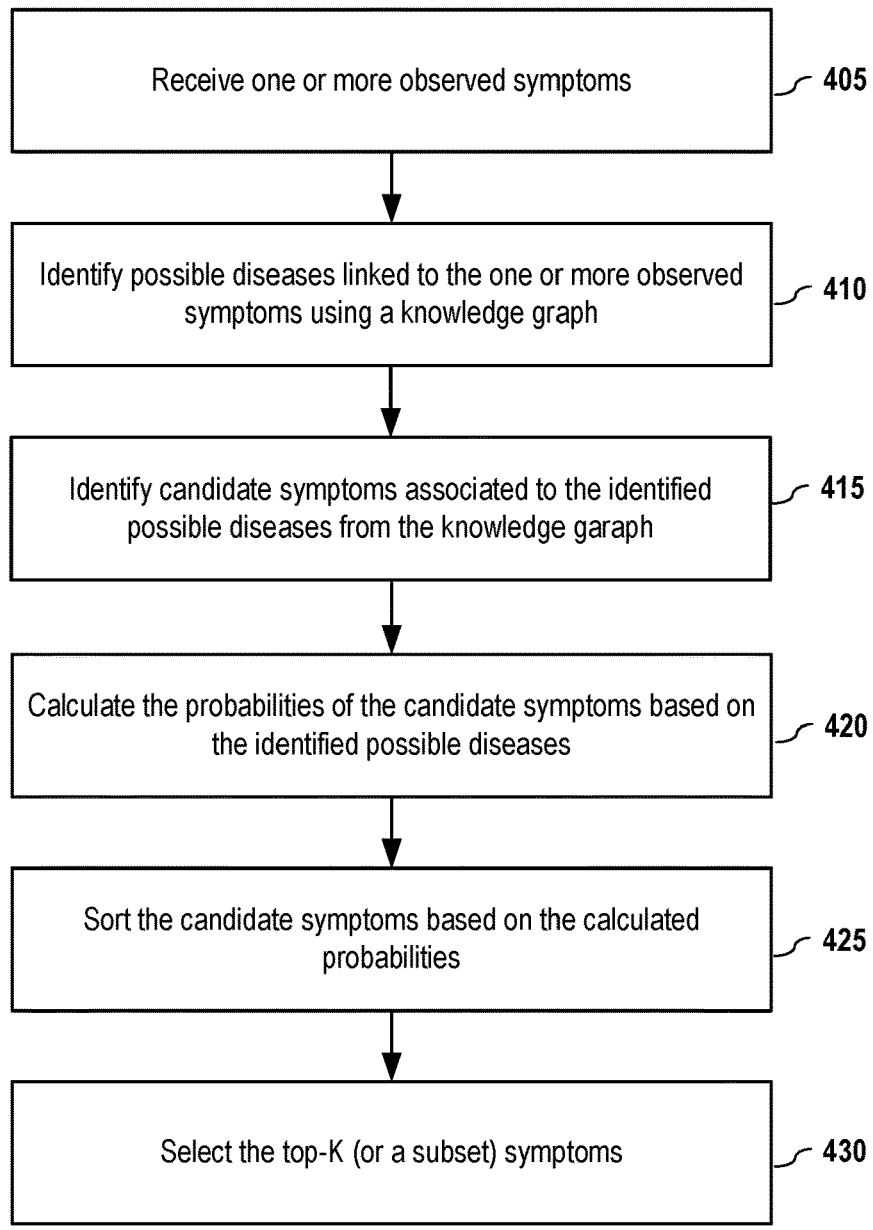
FIG. 4 depicts an exemplary flow diagram of generating candidate symptoms based on observed symptoms according to embodiments of the present disclosure.

FIG. 4 depicts an exemplary flow diagram of generating candidate symptoms based on observed symptoms according to embodiments of the present disclosure. In step 405, one or more observed symptoms ($S_O=\{s_{o_i}\}$, where $s_{o_i}$ represents the ith observed symptom) are received from the patient. In embodiments, at step 410, possible diseases linked to the one or more observed symptoms are identified using the knowledge graph. In embodiments, the most likely diseases may be identified using a graph inference algorithm, such as Markov chain Monte Carlo (MCMC) or Gibbs sampling, etc. In embodiments, the most likely diseases are those diseases that have a probability above a threshold value or it may be the top X number of diseases. In step 415, in embodiments, M (an integer number larger than 1) candidate symptoms ($S_c$) associated with the likely diseases are identified using the knowledge graph. Each candidate symptom may be associate to one or more possible diseases. Similarly, each possible disease may associate to one or more candidate symptoms.

In step 420, the probabilities of the identified candidate symptoms are calculated based on the likely disease. In embodiments, the calculation of the probabilities of a candidate symptoms given the observed symptoms may be given by:

$$\max_{S_c} P(S_c | S_o) \quad (1)$$

wherein $S_o$ is observed symptom(s) and $S_c$ is unobserved or candidate symptom.

In step 425, in embodiments, the identified candidate symptoms are sorted based on the calculated probabilities. In step 430, in embodiments, the top-K candidate symptoms are selected among all identified candidate symptoms as related candidate symptoms. In embodiments, K is a positive integer number less than M.

Figure 5:
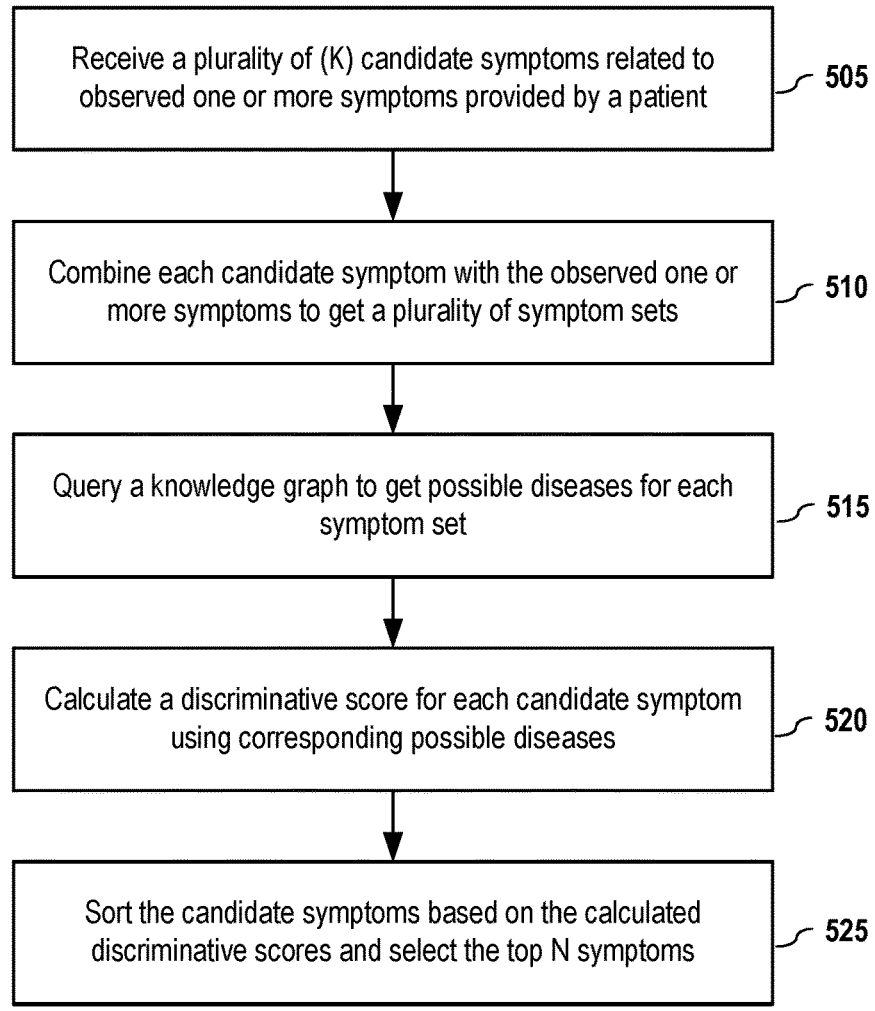
FIG. 5 depicts an exemplary flow diagram of selecting discriminating candidate symptoms according to embodiments of the present disclosure.

FIG. 5 depicts an exemplary flow diagram of selecting a set of discriminating symptoms from candidate symptoms according to embodiments of the present disclosure. In step 505, a plurality (K) of candidate symptoms ($S_c$) are received. In embodiments, the candidate symptoms may be related candidate symptoms pre-selected during processes shown in FIG. 4. In step 510, in embodiments, each candidate symptom is combined with observed symptoms to get a plurality of symptom sets, with each symptom set corresponding to a candidate symptom. In step 515, the symptom sets are used to get likely diseases and unlikely diseases by querying the knowledge graph. Each candidate symptom therefore corresponds to one or more possible diseases. In embodiments, the likely diseases may be identified using a graph inference algorithm, such as Markov chain Monte Carlo (MCMC) or Gibbs sampling, etc. In embodiments, the likely diseases, $D_p$, are those diseases that have a probability above a threshold value or are the top X number of diseases and the remaining diseases (i.e., unlikely diseases) are designated as $D_n$.

In embodiments, when the symptom sets are used to get possible diseases, each symptom within one symptom set is given the same weight in determining possible diseases. In embodiments, each symptom within one symptom set may also be given different weight in determining possible diseases. For example, those life threatening symptoms or symptoms that allows are present may be given more weight in deciding possible diseases than minor or intermittent symptoms.

In step 520, a discriminative (or discriminability) score is calculated for each candidate symptom using corresponding possible diseases. In embodiments, the discriminative score is the maximized probability gap between top likely diseases and unlikely diseases from the possible diseases. In embodiments, the calculation is given by:

$$\max_{S_n} P(D_p, S_o \cup S_n) - P(D_n, S_o \cup S_n) \qquad (2)$$

wherein $S_o$ is the set of observed symptom(s), $S_n$ is a candidate symptom, $D_p$ represents the likely diseases (e.g., top-K diseases) for the combined set of $S_o$ and $S_n$, and $D_n$ represents the unlikely diseases (e.g., non-top-K diseases) for the combined set of $S_o$ and $S_n$. In embodiments, equation (2) may be also maximum across all candidate symptoms based upon likely vs. unlikely disease pairing. That is, for each of the candidate symptoms, equation (2) identifies which candidate symptom is best for differentiating between likely disease $D_{pi}$ versus unlikely disease $D_{nj}$.

In step 525, the candidate symptoms are sorted based on the calculated discriminative scores and the top-N candidate symptoms are selected among the K candidate symptoms as selected candidate symptoms.

Figure 6:
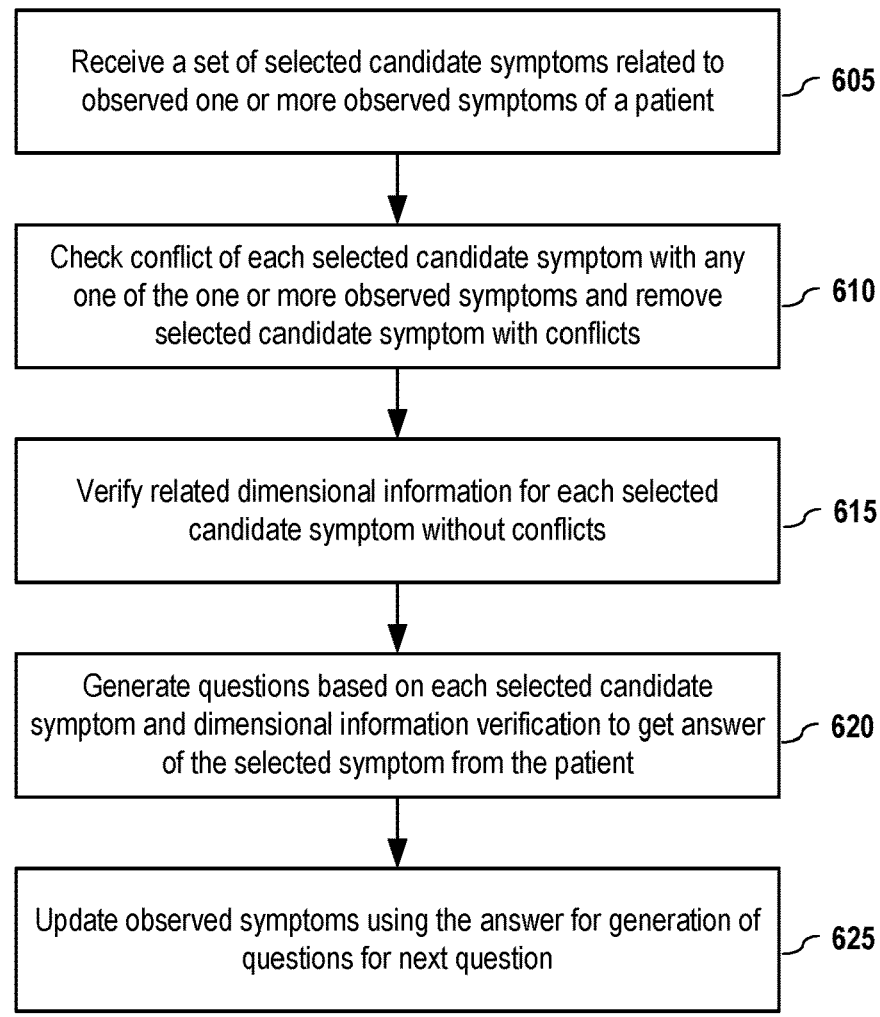
FIG. 6 shows an exemplary flow diagram of candidate symptom filtering and dimensional information verification according to embodiments of the present disclosure.

FIG. 6 shows an exemplary flow diagram of candidate symptom filtering and dimensional information verification according to embodiments of the present disclosure. In step 605, a set of selected candidate symptoms related to observed symptoms of a patient are received. The selected candidate symptoms may be obtained using processes disclosed in FIG. 5. In step 610, in embodiments, each of the selected candidate symptoms is checked for conflict with the observed symptoms and those selected candidate symptoms with conflicts are removed from further consideration. In embodiments, the conflicts are referred as contradictions between the candidate symptoms and observed symptoms. For example, symptoms related to demographics that are inconsistent with the patient may be discarded. In step 615, in embodiments, the selected candidate symptoms without conflicts are checked whether there is related dimensional information. Dimensional information is one or more aspects describing a symptom, such as frequency, intensity, duration, severity, etc. In embodiments, the dimensional aspects may be obtained from a knowledge graph or from other preset data.

In embodiments, in step 620, questions are generated based on the selected candidate symptoms without conflicts. In embodiments, if a symptom has related dimension information, questions related to that dimensional information may also be generated. The questions may be presented to the patient to collect answers.

In embodiments, in step 615, the observed symptoms are updated using the answers for the generated questions, which may be used to generate additional questions by repeating the process and/or for diagnosing a disease. For example, in embodiments, the process may be repeated until no further candidate symptoms are reported from the patient or a disease is diagnosed with a threshold above a confidence level. The confidence level may be a fixed value or a dynamic value based on the disease being diagnosed.

In embodiments, aspects of the present patent document may be directed to or implemented on information handling systems/computing systems. For purposes of this disclosure, a computing system may include any instrumentality or aggregate of instrumentalities operable to compute, calculate, determine, classify, process, transmit, receive, retrieve, originate, route, switch, store, display, communicate, manifest, detect, record, reproduce, handle, or utilize any form of information, intelligence, or data for business, scientific, control, or other purposes. For example, a computing system may be a personal computer (e.g., laptop), tablet computer, phablet, personal digital assistant (PDA), smart phone, smart watch, smart package, server (e.g., blade server or rack server), a network storage device, or any other suitable device and may vary in size, shape, performance, functionality, and price. The computing system may include random access memory (RAM), one or more processing resources such as a central processing unit (CPU) or hardware or software control logic, ROM, and/or other types of memory. Additional components of the computing system may include one or more disk drives, one or more network ports for communicating with external devices as well as various input and output (I/O) devices, such as a keyboard, a mouse, touchscreen and/or a video display. The computing system may also include one or more buses operable to transmit communications between the various hardware components.

Figure 7:
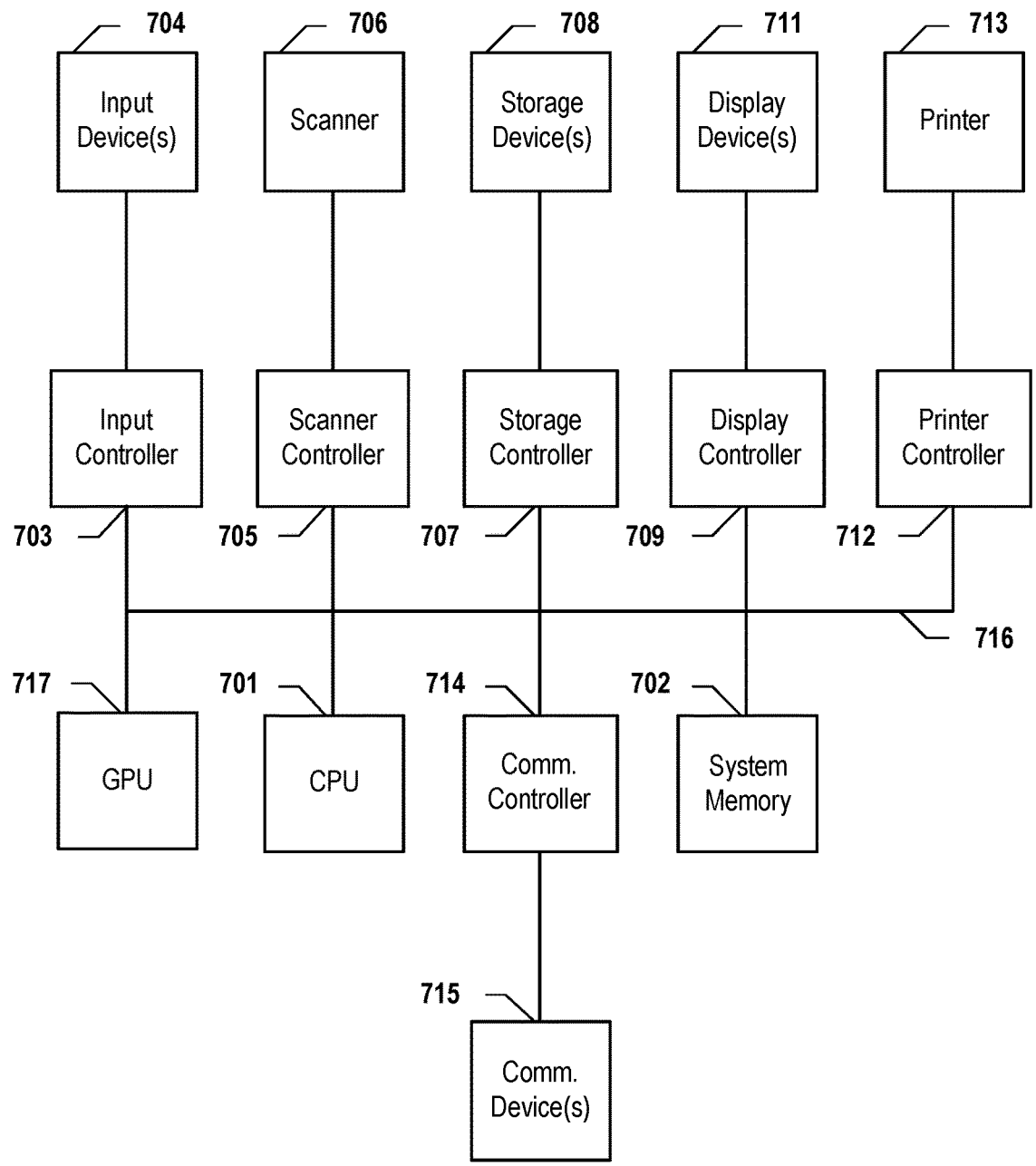
FIG. 7 depicts a simplified block diagram of a computing device/information handling system, in accordance with embodiments of the present disclosure.

FIG. 7 depicts a block diagram of a computing system 700 according to embodiments of the present invention. It will be understood that the functionalities shown for system 700 may operate to support various embodiments of a computing system—although it shall be understood that a computing system may be differently configured and include different components. As illustrated in FIG. 7, system 700 includes one or more central processing units (CPU) 701 that provides computing resources and controls the computer. CPU 701 may be implemented with a microprocessor, microcontroller, or the like, and may also include one or more graphics processing units (GPU) 717 and/or a floating point coprocessor for mathematical computations. System 700 may also include a system memory 702, which may be in the form of random-access memory (RAM), read-only memory (ROM), or both.

A number of controllers and peripheral devices may also be provided, as shown in FIG. 7. An input controller 703 represents an interface to various input device(s) 704, such as a keyboard, mouse, or stylus. There may also be a scanner controller 705, which communicates with a scanner 706. System 700 may also include a storage controller 707 for interfacing with one or more storage devices 708 each of which includes a storage medium such as magnetic tape or disk, or an optical medium that might be used to record programs of instructions for operating systems, utilities, and applications, which may include embodiments of programs that implement various aspects of the present invention. Storage device(s) 708 may also be used to store processed data or data to be processed in accordance with the invention. System 700 may also include a display controller 709 for providing an interface to a display device 711, which may be a cathode ray tube (CRT), a thin film transistor (TFT) display, or other type of display. The computing system 700 may also include a printer controller 712 for communicating with a printer 713. A communications controller 714 may interface with one or more communication devices 715, which enables system 700 to connect to remote devices through any of a variety of networks including the Internet, an Ethernet cloud, a Fibre Channel over Ethernet (FCoE)/Data Center Bridging (DCB) cloud, a local area network (LAN), a wide area network (WAN), a storage area network (SAN) or through any suitable electromagnetic carrier signals including infrared signals.

In the illustrated system, all major system components may connect to a bus 716, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, microcontroller, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It will be appreciated to those skilled in the art that the preceding examples and embodiments are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

It shall be noted that elements of the claims, below, may be arranged differently including having multiple dependencies, configurations, and combinations. For example, in embodiments, the subject matter of various claims may be combined with other claims.

The invention claimed is:

1. A computer-implemented method for improving accuracy of diagnosis, the method comprising:
   receiving as an input a set of observed symptoms comprising at least one observed symptom about a patient;
   generating a set of possible diseases comprising at least one possible disease associated with the set of observed symptoms by querying a knowledge graph that comprises symptom-disease associations, wherein the knowledge graph is generated in which a node in the knowledge graph is either a symptom node that represents a symptom or a disease node that represents a disease and an edge that links a symptom node to a disease node has an associated symptom-disease pair value that represents a probability between the disease represented by the disease node given an observation of the symptom associated with the symptom node and the probabilities of the knowledge graph are generated using an iterative weighted process that iteratively updates at least the probability between symptom-disease pair values in the knowledge graph until a stop condition is reached;

identifying, using the knowledge graph, a plurality of candidate symptoms associated with the set of possible diseases;

determining a discriminative score for each candidate symptom of a set of candidate symptoms from the plurality of candidate symptoms by performing the steps comprising:

combining the candidate symptom with the set of observed symptoms to form a symptom set, wherein each symptom in the symptom set has an associated weight;

using a graph inference model to infer a probability for each disease of a plurality of diseases identified using the knowledge graph and the symptom set, wherein the probability is based, at least in part, upon the associated weights of the symptom set and symptom-disease pair values obtained from the knowledge graph;

forming a set of likely diseases comprising diseases from the plurality of diseases that have a probability above a threshold and a set of unlikely diseases that do not have a probability above the threshold; and determining the discriminative score of the candidate symptom based on a maximized probability gap between at least one or more of the likely diseases from the set of likely diseases associated with the symptom set and at least one or more of the unlikely diseases from the set of unlikely diseases associated with the symptom set;

selecting a subset of candidate symptoms among the plurality of candidate symptoms; and outputting one or more indicia for determining absence or presence of a candidate symptom from the selected subset of candidate symptoms for the patient.

2. The computer-implemented method of claim 1 wherein a candidate symptom in the selected subset of candidate symptoms is checked for one or more conflicts before outputting one or more indicia for determining absence or presence of a candidate symptom from the selected subset of candidate symptoms for the patient.

3. The computer-implemented method of claim 2 wherein any candidate symptom with one or more conflicts is removed from the selected subset.

4. The computer-implemented method of claim 2 wherein the selected candidate symptoms without conflicts are further checked for dimensional information.

5. The computer-implemented method of claim 4 wherein the dimensional information comprises one or more aspects describing the selected candidate symptom.

6. The computer-implemented method of claim 1 further comprising updating the observed symptoms after information about the selected subset of candidate symptoms being collected.

7. A system for improving disease diagnosis, the system comprising:

one or more processors;

a knowledge graph accessible by the one or more processors, wherein the knowledge graph was generated in which a node in the knowledge graph is either a symptom node that represents a symptom or a disease node that represents a disease and an edge that links a symptom node to a disease node has an associated symptom-disease pair score that represents a probability between the disease represented by the disease node given an observation of the symptom associated with the symptom node and the probabilities of the knowledge graph are generated using an iterative weighted process that iteratively updates the probability between symptom-disease pair scores in the knowledge graph until a stop condition is reached;

a non-transitory computer-readable medium or media comprising one or more sequences of instructions which, when executed by at least one processor of the one or more processors, causes the steps to be performed:

using a set of observed symptoms of a patient and a knowledge graph that associated symptoms and diseases to identify a set of candidate symptoms related to a set of possible diseases that are related to the set of observed symptoms of the patient;

combining each candidate symptom with the set of observed symptoms to get a plurality of symptom sets with each symptom set corresponding to one candidate symptom, wherein each symptom in a symptom set has an associated weight;

for each symptom set, using a graph inference model to infer a probability for each disease of a plurality of diseases identified using the knowledge graph, wherein the probability is based, at least in part, upon the associated weights of the symptom set and symptom-disease pair values obtained from the knowledge graph;

forming, for each candidate symptom, a set of likely diseases comprising diseases from the plurality of diseases that have a probability above a threshold and a set of unlikely diseases that do not have a probability above the threshold;

determining a discriminative score for each candidate symptom using the set of likely diseases and the set of unlikely diseases by maximizing a different between a probability of one or more diseases from the set of likely diseases for a symptom set and a probability of one or more diseases from the set of unlikely diseases for a symptom set; and selecting a subset of candidate symptoms from the set of candidate symptoms based upon discriminative score.

8. The system of claim 7 wherein a candidate symptom from the subset of candidate symptoms is checked for one or more conflicts before generating questions for determining absence or presence of the candidate symptom for the patient.

9. The system of claim 8 wherein the subset of candidate symptoms without conflicts are further checked for dimensional information.

10. The system of claim 9 wherein the dimensional information comprises one or more aspects related the candidate symptom.

11. The system of claim 8 further comprising:

generating one or more questions related to one or more candidate symptoms from the subset of candidate symptoms without conflicts for use in collecting additional information to help diagnosis the patient.

12. A system for improving diagnosis comprising:

an input interface to receive data about at least one observed symptom from a patient;

an output interface to send questions to the patient;

one or more processors coupled to the input interface and the output interface; and a non-transitory computer-readable medium or media comprising one or more sequences of instructions which, when executed by at least one of the one or more processors, causes the steps to be performed:

obtaining a set of observed symptoms comprising at least one observed symptom about a patient;

generating a set of possible diseases comprising at least one possible disease associated with the set of observed symptoms by querying a knowledge graph that comprises symptom-disease associations, wherein the knowledge graph was generated in which a node in the knowledge graph is either a symptom node that represents a symptom or a disease node that represents a disease and an edge that links a symptom node to a disease node has an associated symptom-disease pair value that represents a probability between the disease represented by the disease node given an observation of the symptom associated with the symptom node and the probabilities of the knowledge graph are generated using an iterative weighted process that iteratively updates at least the probability between symptom-disease pair values in the knowledge graph until a stop condition is reached;

identifying a plurality of candidate symptoms associated with the set of possible diseases;

determining a discriminative score for each candidate symptom of a set of candidate symptoms from the plurality of candidate symptoms by performing the steps comprising:

combining the candidate symptom with the set of observed symptoms to form a symptom set, wherein each symptom in the symptom set has an associated weight;

using a graph inference to infer a probability for each disease of a plurality of diseases identified using the knowledge graph and the symptom set, wherein the probability is based, at least in part, upon the associated weights of the symptom set and symptom-disease pair values obtained from the knowledge graph;

forming a set of likely diseases comprising diseases from the plurality of diseases that have a probability above a threshold and a set of unlikely diseases that do not have a probability above the threshold; and selecting a subset of candidate symptoms among the plurality of candidate symptoms based on the discriminative scores; and outputting one or more indicia for determining absence or presence of a candidate symptom from the selected subset of candidate symptoms for the patient.

13. The system of claim 12 wherein the step of outputting one or more indicia for determining absence or presence of a candidate symptom from the selected subset of candidate symptoms comprises generating questions for one or more candidate symptoms from the selected subset of candidate symptoms to collect information.

14. The system of claim 12 wherein the step of identifying a plurality of candidate symptoms associated with the at least one possible disease comprises using a graph inference on the knowledge graph.

15. The system of claim 14 wherein the graph inference comprises using at least one of a Markov Chain Monte Carlo (MCMC) sampling and Gibbs sampling.

16. The system of claim 12 wherein a candidate symptom in the selected subset of candidate symptoms is checked for one or more conflicts before outputting the one or more indicia for determining absence or presence of a candidate symptom from the selected subset of candidate symptoms.

17. The system of claim 16 wherein any candidate symptom with conflicts is removed from the selected subset.

18. The computer-implemented method of claim 1 wherein the step of outputting one or more indicia for determining absence or presence of a candidate symptom from the selected subset of candidate symptoms for the patient comprises generating one or more prompts for information to aid in determining absence or presence of a candidate symptom from the selected subset of candidate symptoms.

19. The system of claim 7 further comprising outputting one or more indicia for determining absence or presence of a candidate symptom from the selected subset of candidate symptoms for the patient.

* * * * *